United States Patent
Zhang

(10) Patent No.: US 9,320,445 B2
(45) Date of Patent: Apr. 26, 2016

(54) SYSTEM FOR CARDIAC CONDITION DETECTION RESPONSIVE TO BLOOD PRESSURE ANALYSIS

(75) Inventor: Hongxuan Zhang, Palatine, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 175 days.

(21) Appl. No.: 13/215,311

(22) Filed: Aug. 23, 2011

(65) Prior Publication Data

US 2012/0296225 A1 Nov. 22, 2012

Related U.S. Application Data

(60) Provisional application No. 61/486,845, filed on May 17, 2011.

(51) Int. Cl.

| A61B 5/02 | (2006.01) |
| A61B 5/021 | (2006.01) |
| A61B 5/00 | (2006.01) |
| G06F 19/00 | (2011.01) |

(52) U.S. Cl.
CPC ............. *A61B 5/021* (2013.01); *A61B 5/7264* (2013.01); *G06F 19/345* (2013.01)

(58) Field of Classification Search
CPC ..... A61B 5/021; A61B 5/7264; G06F 19/345
USPC ................. 600/373–375, 449–450, 481–503, 600/508–528
See application file for complete search history.

(56) References Cited

U.S. PATENT DOCUMENTS

| 4,566,463 | A |   | 1/1986 | Taniguchi et al. |   |
|---|---|---|---|---|---|
| 5,279,303 | A |   | 1/1994 | Kawamura et al. |   |
| 5,423,326 | A |   | 6/1995 | Wang et al. |   |
| 5,615,684 | A |   | 4/1997 | Hagel et al. |   |
| 5,752,919 | A |   | 5/1998 | Schrimpf |   |
| 5,817,027 | A | * | 10/1998 | Arand et al. | 600/515 |
| 6,007,491 | A |   | 12/1999 | Ling et al. |   |
| 6,050,951 | A |   | 4/2000 | Friedman et al. |   |

(Continued)

OTHER PUBLICATIONS

K. Laederach-Hofmann et al., "Early Autonomic Dysfunction in Patients with *Diabetes mellitus* Assessed by Spectral Analysis of Heart Rate and Blood Pressure Variability", Clinical Physiology 19, 2, 97-106, 1999 Blackwell Science Ltd.

(Continued)

*Primary Examiner* — Niketa Patel
*Assistant Examiner* — Lindsey G Hankins

(57) ABSTRACT

A system provides cardiac arrhythmia detection and performs blood pressure analysis of multiple catheter channels of blood pressure signals to characterize heart hemodynamic activity. A system for heart performance characterization and abnormality detection includes a repository, data processor and output processor. The repository of data comprises, first distribution data representing a probability distribution of a first patient parameter over a first time period and acquired on a first occasion and second distribution data representing a probability distribution of the first patient parameter over a second time period and acquired on a second occasion subsequent to the first occasion. The data processor calculates an overlap indicator indicating degree of overlap of the first distribution data and the second distribution data in a predetermined interval of the distributions. The output processor provides the calculated overlap indicator to a destination device.

18 Claims, 11 Drawing Sheets

(56) References Cited

U.S. PATENT DOCUMENTS

| | | |
|---|---|---|
| 6,071,244 A | 6/2000 | Band et al. |
| 6,117,075 A | 9/2000 | Barnea |
| 6,179,783 B1 | 1/2001 | Mohler |
| 6,186,956 B1 | 2/2001 | McNamee |
| 6,224,553 B1 | 5/2001 | Nevo |
| 6,308,098 B1 | 10/2001 | Meyer |
| 6,348,038 B1 | 2/2002 | Band et al. |
| 6,485,429 B2 | 11/2002 | Forstner |
| 6,490,480 B1 | 12/2002 | Lerner |
| 6,511,436 B1 | 1/2003 | Asmar |
| 6,511,438 B2 | 1/2003 | Bernstein et al. |
| 6,514,211 B1 | 2/2003 | Baura |
| 6,616,613 B1 | 9/2003 | Goodman |
| 6,636,754 B1 | 10/2003 | Baura et al. |
| 6,758,822 B2 | 7/2004 | Romano |
| 6,929,610 B2 | 8/2005 | Forstner |
| 7,024,244 B2 | 4/2006 | Muhlenberg et al. |
| 7,074,192 B2 | 7/2006 | Friedman et al. |
| 7,079,888 B2 | 7/2006 | Oung et al. |
| 7,220,230 B2 | 5/2007 | Roteliuk et al. |
| 7,367,949 B2 | 5/2008 | Korhonen et al. |
| 7,374,541 B2 | 5/2008 | Amitzur et al. |
| 7,384,395 B2 | 6/2008 | Hatlestsad et al. |
| 7,413,548 B2 | 8/2008 | Tadokoro et al. |
| 7,503,896 B2 | 3/2009 | Miele et al. |
| 7,704,209 B2 | 4/2010 | Bennett et al. |
| 2003/0229289 A1 * | 12/2003 | Mohler et al. ............ 600/508 |
| 2009/0209868 A1 | 8/2009 | Hersh et al. |
| 2010/0152593 A1 | 6/2010 | Lowe |
| 2010/0204591 A1 | 8/2010 | Hatib et al. |
| 2010/0204592 A1 | 8/2010 | Hatib et al. |
| 2010/0280396 A1 | 11/2010 | Zhang |

OTHER PUBLICATIONS

Benno Nafz, et al., "Endogenous Nitric Oxide Buffers Blood Pressure Variability Between 0.2 and 0.6 Hz in the Conscious Rat", American Journal of Physiology (Heart Circulation Physiology), 272: H632-H637, 1997.

Pelat, et al., "Rosuvastatin Decreases Caveolin-1 and Improves Nitric Oxide-Dependent Heart Rate and Blood Pressure Variability in Apolipoprotein E-/- Mice In Vivo", Circulation, Journal of the American Heart Association, 107: 2480-2486, 2003.

G. Parati, et al., "Neural Cardiovascular Regulation and 24-Hour Blood Pressure and Heart Rate Variability", Annals of the New York Academy of Sciences, 783:47-63, 1996.

Wei Huang, et al., "Engineering analysis of biological variables: An example of blood pressure over 1 day", PNAS Apr. 28, 1998, vol. 95 No. 9, p. 4816-4821.

* cited by examiner

Figure 5

| Time | Normal | | Pathology 1 | | Pathology 2 (severe) | |
|---|---|---|---|---|---|---|
| | Averaging BP and Heart rate | Standard deviation of BP | Averaging BP and Heart rate | Standard deviation of BP | Averaging BP and Heart rate | Standard deviation of BP |
| T1 | BP=120 HR=70 | 4 | BP=110 HR=75 | 6 | BP=101 HR=75 | 9 |
| T2 | BP=121 HR=70 | 4 | BP=108 HR=75 | 8 | BP=99 HR=78 | 8 |

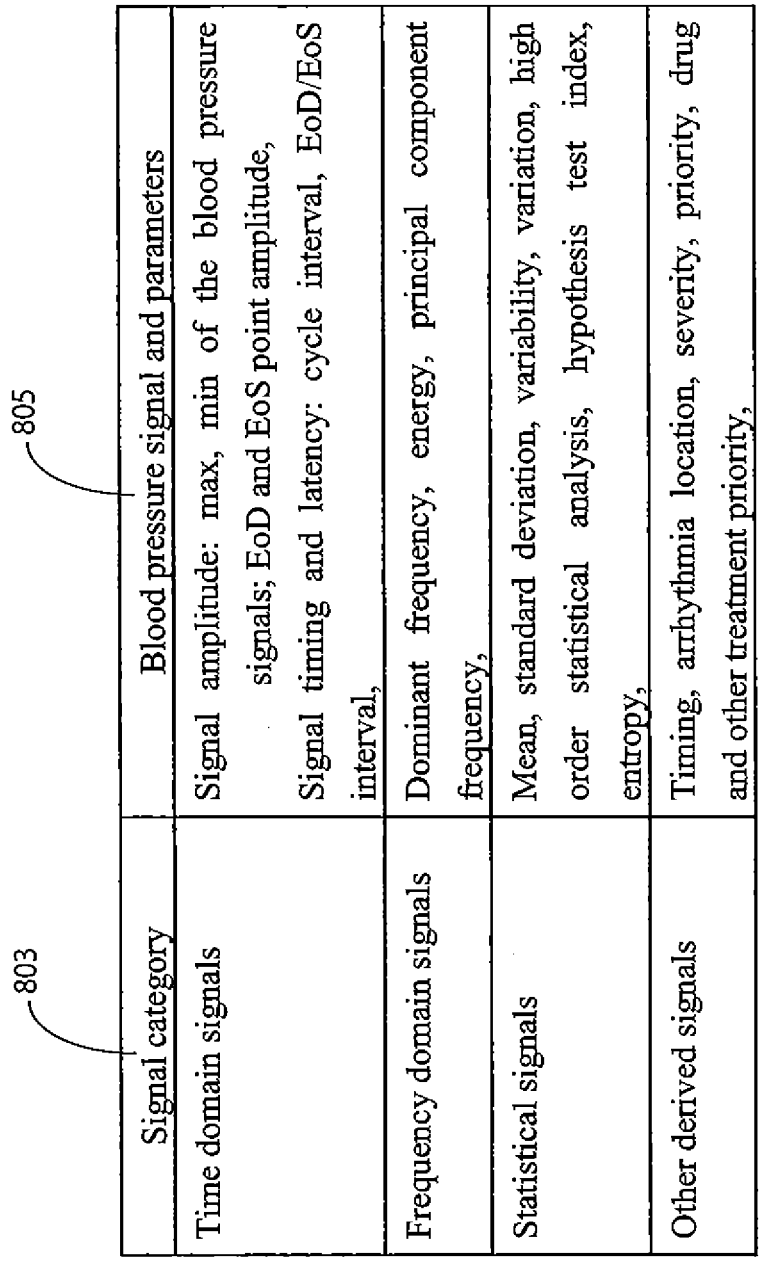

Figure 8

| Signal category | Blood pressure signal and parameters |
|---|---|
| Time domain signals | Signal amplitude: max, min of the blood pressure signals; EoD and EoS point amplitude, Signal timing and latency: cycle interval, EoD/EoS interval, |
| Frequency domain signals | Dominant frequency, energy, principal component frequency, |
| Statistical signals | Mean, standard deviation, variability, variation, high order statistical analysis, hypothesis test index, entropy, |
| Other derived signals | Timing, arrhythmia location, severity, priority, drug and other treatment priority, |

US 9,320,445 B2

SYSTEM FOR CARDIAC CONDITION DETECTION RESPONSIVE TO BLOOD PRESSURE ANALYSIS

This is a non-provisional application of provisional application Ser. No. 61/486,845 filed May 17, 2011, by H. Zhang.

FIELD OF THE INVENTION

This invention concerns a system for heart performance characterization and abnormality detection involving calculating an overlap indicator indicating degree of overlap of different probability distributions of a patient parameter over different time periods and acquired on different occasions, for example.

BACKGROUND OF THE INVENTION

Blood pressure (BP) is a measurement of the force applied to the walls of arteries as the heart pumps blood through the body and is determined by the force and amount of blood pumped, and the size and flexibility of the arteries. Types of blood pressure include systolic and diastolic types. The systolic blood pressure corresponds to the pressure of blood when the heart has imparted the maximum pressure. The diastolic blood pressure is the pressure when the heart is in the resting phase. Systolic and diastolic arterial BP is not static but undergoes natural variations from one heartbeat to another and throughout the day (in a circadian rhythm). Known systems use power spectrum information (such as in a Low or High Frequency bandwidth) to analyze blood pressure variability for detecting cardiac abnormality. However, blood pressure variability may be affected by many factors, such as age, disease, breathing control, physical condition, neurological status.

Know clinical methods for blood pressure waveform characterization typically require extensive clinical experience and knowledge. Known clinical methods are typically unable to detect early small changes in blood pressure magnitude from pressure waveform data. Known cardiac function analysis systems typically analyze an electrophysiological signal. However an electrophysiological signal is easily distorted and affected by electrical noise and biological artifacts, such as power line noise and patient movement. Known systems also fail to provide hemodynamic quantitative analysis for implantable cardiac devices (ICDs). A system according to invention principles addresses these deficiencies and related problems.

SUMMARY OF THE INVENTION

A system provides cardiac arrhythmia and pathology detection and diagnosis in response to blood pressure signal data by dynamic signal pattern analysis of blood pressure waveform data. A system for heart performance characterization and abnormality detection includes a repository, data processor and output processor. The repository of data comprises, first distribution data representing a probability distribution of a first patient parameter over a first time period and acquired on a first occasion and second distribution data representing a probability distribution of the first patient parameter over a second time period and acquired on a second occasion subsequent to the first occasion. The data processor calculates an overlap indicator indicating degree of overlap of the first distribution data and the second distribution data in a predetermined interval of the distributions. The output processor provides the calculated overlap indicator to a destination device.

BRIEF DESCRIPTION OF THE DRAWING

FIG. 5 comprises a table showing normal blood pressure data, first pathology blood pressure data, and second pathology blood pressure data, acquired at different times, according to invention principles.

FIG. 8 comprises a table listing blood pressure signals and associated derived parameters used for blood pressure analysis, according to invention principles.

DETAILED DESCRIPTION OF THE INVENTION

A system provides cardiac condition (e.g., arrhythmia) detection and characterization in response to blood pressure dynamic signal pattern analysis. In one embodiment the system combines blood pressure analysis (including use of timing parameters, blood pressure based morphology indicators, frequency related parameters and statistical analysis) derived from multiple catheter channels to detect and quantify heart hemodynamic activity and cardiac arrhythmia severity. The system analyzes and monitors blood pressure signal patterns to determine time, location and severity of cardiac pathology events. The system further identifies cardiac disorders, differentiates between types of cardiac arrhythmias, characterizes pathological severity, predicts life-threatening events, and evaluates drug delivery effects.

Figure 1:
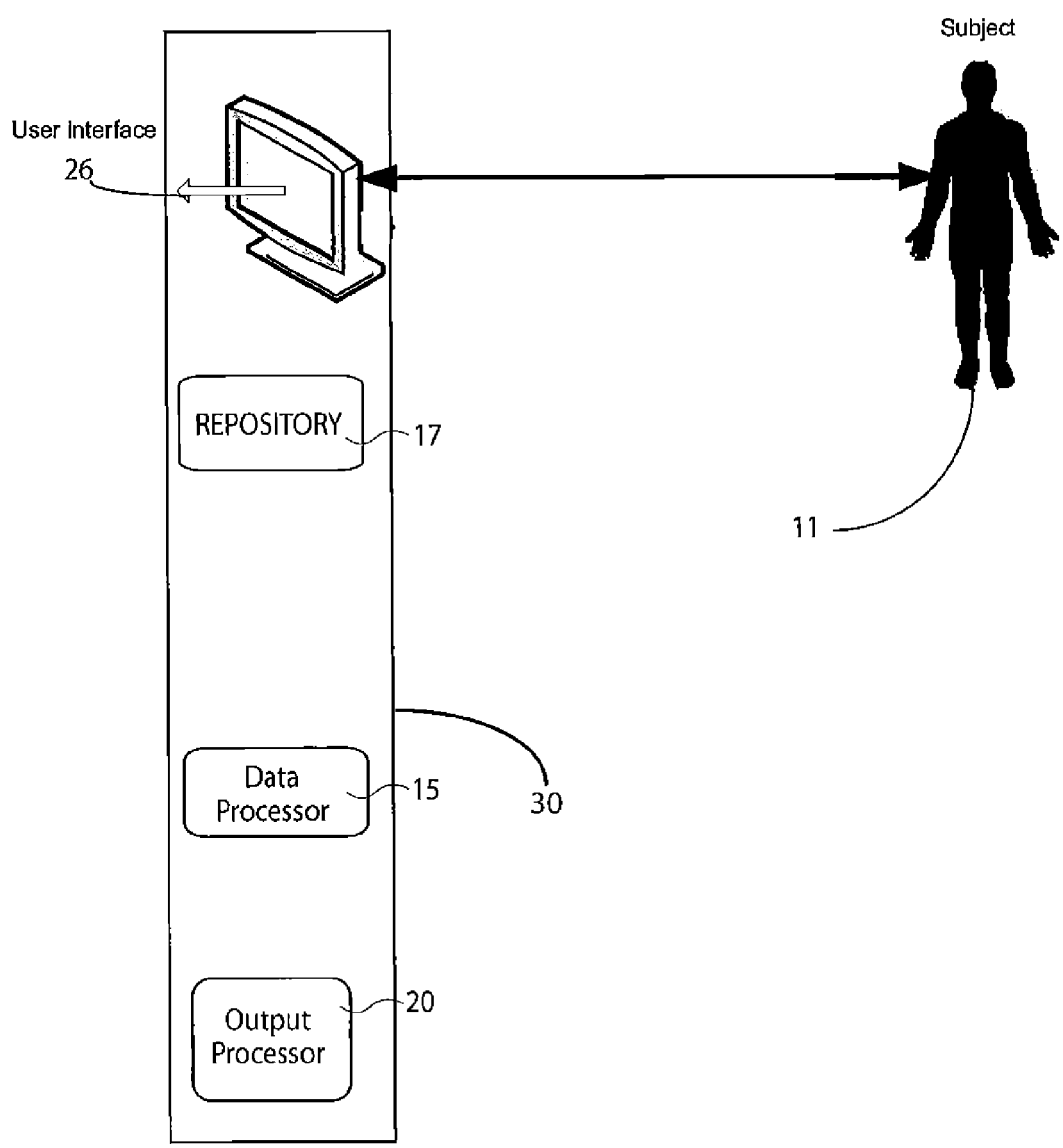
FIG. 1 shows a system for heart performance characterization and abnormality detection, according to invention principles.

FIG. 1 shows system 10 for heart performance characterization and abnormality detection. System 10 comprises at least one computer system, workstation, server or other processing device 30 including repository 17, data processor 15, output processor 20 and a user interface 26. Repository of data 17 comprises, first distribution data representing a probability distribution of a first patient parameter over a first time period and acquired on a first occasion and second distribution data representing a probability distribution of the first patient parameter over a second time period and acquired on a second occasion subsequent to the first occasion. Data processor 15 calculates an overlap indicator indicating degree of overlap of the first distribution data and the second distribution data in a predetermined interval of the distributions. Output processor 20 provides the calculated overlap indicator to a destination device. System determines patient arrhythmia location, type, severity, suggests treatment site priority, and treatment by integrating patient demographic data and patient vital signs data, current clinical diagnosis parameters and an overlap indicator.

Figure 2:
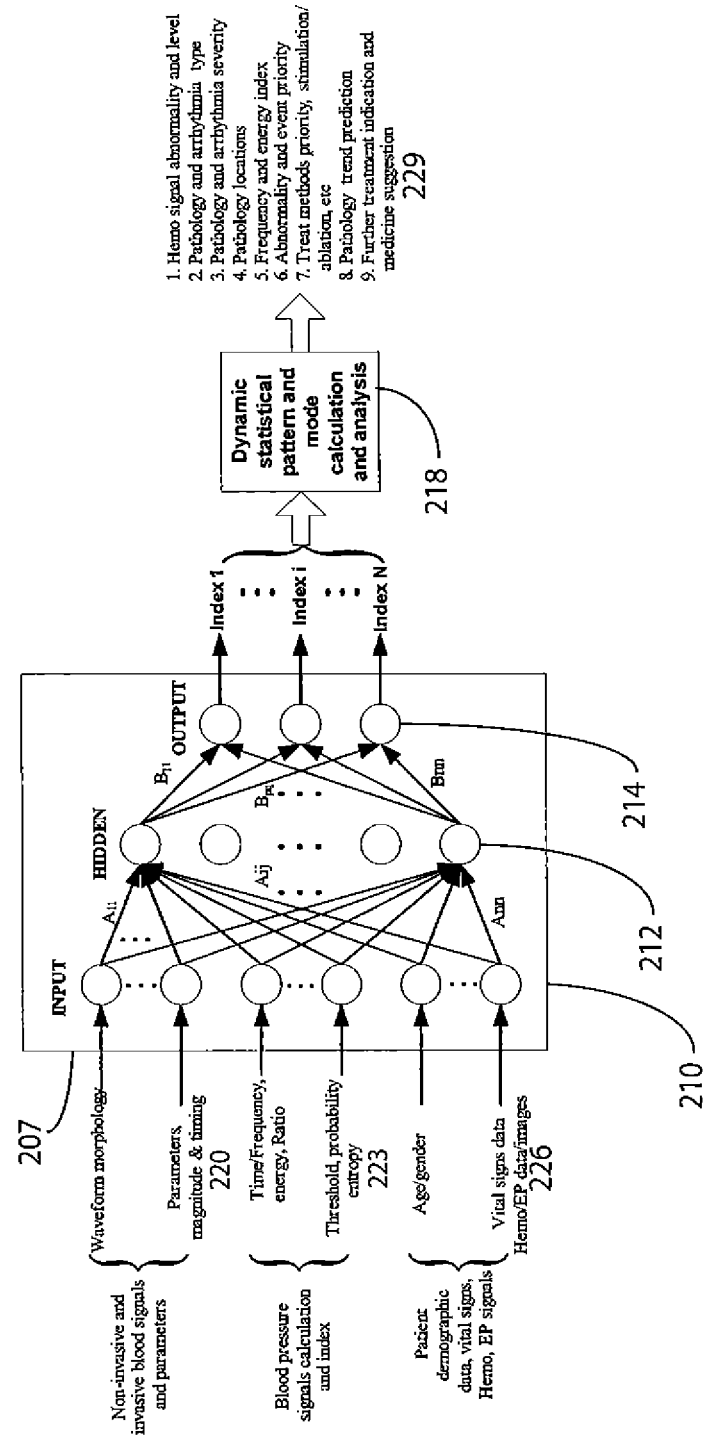
FIG. 2 shows an artificial neural network (ANN) for hemodynamic (invasive and non-invasive blood pressure) data and signal waveform analysis for heart function characterization, according to invention principles.

FIG. 2 shows an artificial neural network (ANN) 207 for hemodynamic (invasive and non-invasive blood pressure) data and signal waveform analysis for heart function characterization. ANN unit 207 integrates and nonlinearly combines multiple kinds of patient information since different types of patient data and data patterns may have a nonlinear relationship. ANN unit 207 comprises a three layer architecture for combining and integrating different kinds of blood pressure measurements, demographic signals, vital signs and ECG signals, for example. ANN unit 207 combines or maps one or more calculated non-invasive and invasive blood pressure signals and parameters 220 (including waveform morphology, magnitude and timing data), calculated blood pressure related values 223 (including time, frequency, energy, entropy and probability distribution data values) and patient demographic data, vital sign, hemodynamic and EP signal data 226, to output parameters 229 via calculation unit 218. Unit 207 employs different methods for patient signal measurement, calculation and estimation including time domain signal waveform analysis, frequency domain parameter calculation, energy calculation, statistical probability and entropy analysis, and vital sign/electrophysiological signal analysis. Measurements and calculations are combined nonlinearly to derive a severity indicator and pathology indicator. The indicators are used in performing statistical tests and validation to identify a dynamic statistical pattern for blood pressure signal pattern quantification and patient cardiac arrhythmia characterization.

Unit 218 processes parameters provided by ANN unit 207 by performing statistical analysis and calculations using the parameters to provide output parameters 229. The ANN unit combines signal analysis results, patient history and physician data and performs pattern analysis to characterize hemodynamic information for a patient including determining pathology severity, location, treatment priorities and an event trend. The output parameters 229 indicate blood pressure signal abnormality level, pathology and arrhythmia type and severity, pathology tissue location, frequency and energy related abnormality parameters, an abnormality and event priority, treatment site ablation or stimulation priority, pathological trend identifier and suggested candidate treatment and medication. ANN unit 207 structure comprises 3 layers, an input layer 210, hidden layer 212 and output layer 214. ANN unit $A_{ij}$ weights are applied between input layer 210 and hidden layer 212 components of the ANN computation and $B_{pq}$ weights are applied between hidden layer 212 and calculation components 214 of the ANN computation. The $A_{ij}$ weights and $B_{pq}$ weights are adaptively adjusted and tuned using a training data set. ANN unit 207 incorporates a self-learning function that processes signals 220, 223 and 226 to increase the accuracy of calculated results.

ANN unit 207 maps input signals 220, 223 and 226 to a candidate diagnosis or treatment suggestion 229 to localize tissue impairment within an organ and determine time of occurrence within a heart cycle. ANN unit 207 also identifies arrhythmia type (e.g., AF, MI, VT, VF), severity of arrhythmia treatment and urgency level and is usable for automatic heart condition detection, diagnosis, warning and treatment. Further unit 207 performs statistical analysis to construct a threshold used to detect tissue impairment and diagnose and predict cardiac arrhythmia and pathology.

Following a training phase with a training data set, ANN unit 207 maps signals 220, 223 and 226 to data 229 indicating an Arrhythmia type, Arrhythmia severity, candidate treatment suggestions, localized tissue impairment information identifying the cardiac arrhythmia position, abnormal tissue area and focus of the disorder and irregularity, for example. The severity threshold of a pathology mapping decision may vary from person to person and is adjusted at the beginning of analysis. The system may be advantageously utilized in general patient monitoring and implantable cardiac devices for real time automatic analysis and detection of cardiac arrhythmias and abnormalities. ANN unit 207 is particularly useful in multi-channel blood pressure pattern analysis, for cross channel comparison and to further define arrhythmia type and location.

Different types of signal measurements and derived parameters in one embodiment are used independently to determine patient status based on blood pressure cycle interval reflecting cardiac reperfusion rate, a blood pressure waveform integration parameter indicating stroke volume and blood pressure waveform morphology statistics indicating blood perfusion and contraction regularity. ANN unit 207 (and data processor 15) in one embodiment calculates nonlinear signal parameter, $$\text{index\_i} = \sum_{j \in \Omega} \alpha_{ij}(t) \cdot C_j$$

where index_i is an output index from ANN unit 207 representing pathology severity, location and timing, $C_j$ represents a parameter derived from the blood pressure signals, other calculations, and other inputs of the ANN unit, $\alpha_{ij}(t)$ represents weights and coefficients. $C_j$ and $\alpha_{ij}(t)$ may be adaptively selected in response to procedure type and patient medical condition indicator. In ANN unit 207, $\alpha_{ij}(t)$ may be derived in response to a training data set, a represents the inputs, including direct patient signal measurements, calculated index, user input and patient demographic data. In a clinical application, different indices may be named according to the meaning and application purpose, such as pathology severity index_1, arrhythmia location index index_2, probability of arrhythmia occurrence index_3, arrhythmia type index_4, EOS (end-of systole) phase interval index_5, blood pressure cycle index_6, domain frequency value index_7 and warning and treatment priority index_8. A dynamic signal pattern indicator is calculated from multiple parameters to indicate a statistical probability and level of patient pathology, event timing, drug delivery effects and to predict a malfunction trend and potential clinical treatment.

In different clinical procedures and different heart rhythms, an index typically shows different values and distribution (indicated by mean value and standard deviation). The system determines a sequential calculation value indicating severity, type, timing and priority, for example. Unit 207 (or processor 15) employs a shifting window (determined by unit 207 or 15 adaptively and automatically in response to sensitivity and noise within data) for processing a sequential index data series for index_1, S1, for example. A ten data point window is used in one embodiment. For each window, a mean value mean(S1), standard deviation STD(S1), variation and variability are calculated using, Mean or averaging value (expectation);

$$\text{mean}(X) = \frac{1}{N} \sum_{i \in N} X(i);$$

Standard deviation:

$$STD(X) = \frac{1}{N-1} \sum_{i \in N-1} (X(i) - \text{mean}(X))$$

$$\text{Signal Variation} = \frac{\text{mean}(X)}{STD(X)}$$

$$\text{Signal Variability} = \frac{\max(X - \text{mean}(X))}{\text{mean}(X)}$$

where X is a parameter and N is a calculation window size (there are N samples in a shifting calculation window).

Figure 3:
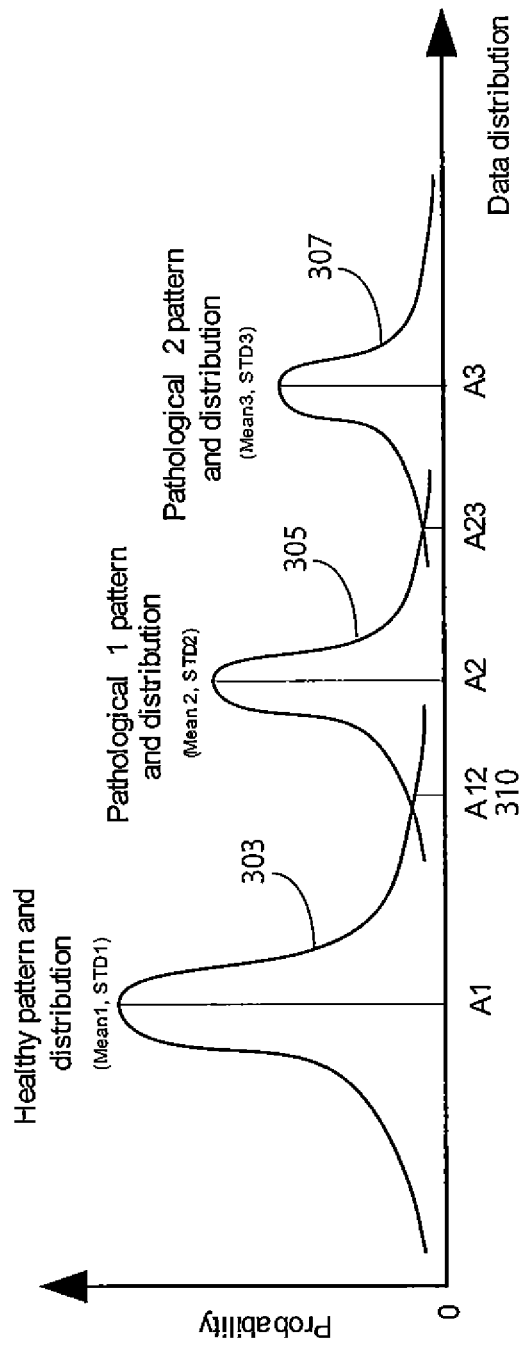
FIG. 3 shows three different probability distribution patterns for a normal blood pressure, a first pathological blood pressure, and a second pathological blood pressure respectively, according to invention principles.
Figure 4:
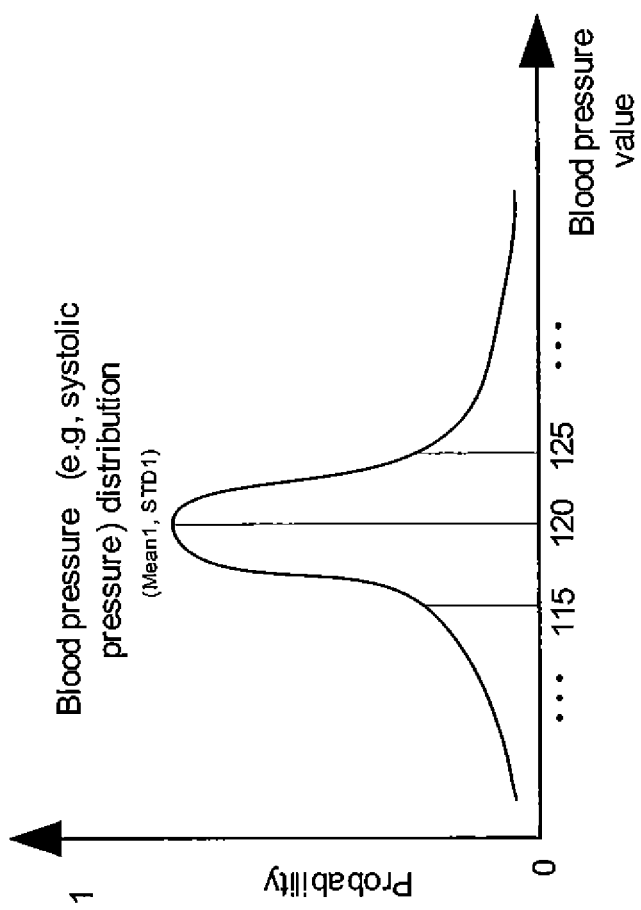
FIG. 4 shows a Gaussian distribution for blood pressure modeling selected for data distribution analysis, according to invention principles.

FIG. 3 shows three different Gaussian probability distribution patterns 303, 305 and 307 for a normal blood pressure, a first pathological blood pressure, and a second pathological blood pressure respectively. Probability signal distribution 303 represents normal pressure, distribution 305 represents a first pathology and distribution 307 represents a second pathology. For example, the first pathology may represent an early stage of myocardial ischemia and the second pathology may represent myocardial infarction. Data processor 15 calculates a signal pattern indicative index value used to detect a likelihood of an of an emerging cardiac arrhythmia or clinical event. In FIG. 3, Ai (A1, A2, A3) represents a mean value of each distribution and Aij (A12, A23) represents a common value intersection point of the two distributions, for example A12 is an intersection point of distributions 303 and 305. System 10 (FIG. 1) may use different models for the blood pressure data distributions, such as a Gaussian distribution, normal distribution, Poisson distribution, Cauchy distribution, T distribution, F distribution, Gamma distribution, a histogram probability function, binomial probability function and cumulative probability function, for example. Data processor 15 adaptively selects a Gaussian distribution for blood pressure modeling and data distribution analysis in this example. FIG. 4 shows a Gaussian probability distribution (range 0 to 1) for systolic blood pressure having a mean value of blood pressure of 120 selected for data distribution analysis by processor 15.

FIG. 5 comprises a lookup table showing normal blood pressure data 503, first pathology blood pressure data 505, and second pathology blood pressure data 507 acquired at different times T1 and T2 corresponding to rows 510 and 512. The blood pressure data includes an average blood pressure value and heart rate and a standard deviation value time stamped with times T1 or T2. In another embodiment, a physiological parameter other than blood pressure or a derived calculated value may be analyzed. Data processor 15 analyzes different patient parameters and data, including EP, Hemodynamic, Vital signs, blood oxygen saturation (SPO2) and temperature data that is directly measured or indirectly calculated and derived, in pattern analysis and patient pathology detection. Processor 15 may employ a maximum value and amplitude of a blood pressure waveform in analysis, or blood pressures of other regions of interest, such as an EOD (end-of-diastolic) pressure or EOS (end-of-systolic) pressure or minimum pressure. A parameter used for analysis is selected in response to at least one of, patient medical condition, user entered data and signal noise level. For example, where a NIBP (non-invasive blood pressure) or respiration signal cannot be reliably detected and measured, IBP or SPO2 signals are adaptively selected for analysis. Blood pressure, and other parameters listed in the Table of FIG. 5 are used for calculation and diagnosis of patient status, for example.

Figure 6:
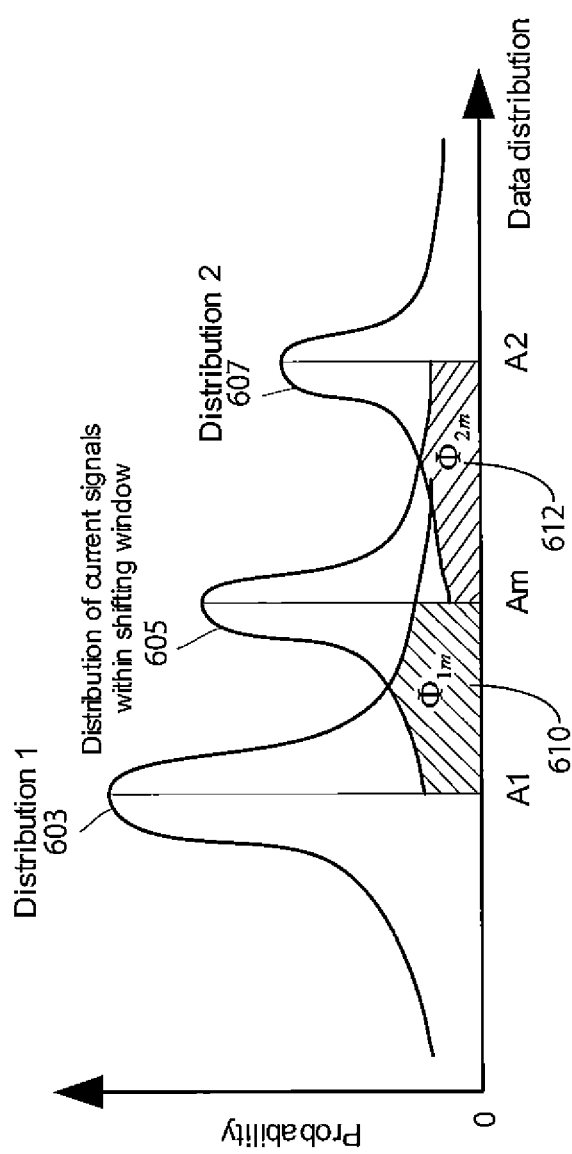
FIG. 6 shows calculated normal, real time and abnormal blood pressure probability distributions illustrating analysis of overlap between distributions, according to invention principles.

FIG. 6 shows calculated normal 603, real time 605 and abnormal 607 blood pressure probability distributions illustrating analysis of overlap between distributions. Multiple different distributions may be used for determining a single parameter to detect arrhythmia type and arrhythmia location. In an example involving a left anterior descending coronary artery (LAD), if myocardial ischemia or infarction occurs at a first branch, it is a first pathological distribution, if it occurs at a second branch, it is a second pathological distribution. A calculated pattern is used for arrhythmia location detection, arrhythmia evaluation and prediction and determination of event timing in a heart cycle and candidate treatment. FIG. 6 illustrates calculation of a blood pressure index value reflecting a comparison of two pre-determined data distributions comprising a (normal) health status and an (abnormal) pathological health status. The mean values of normal 603, real time 605 and abnormal 607 distribution are A1, Am and A2 respectively. Data processor 15 determines an overlap area between two distributions such as $\Phi_{1m}$, and $\Phi_{2m}$. The calculated overlap area index comprises an index representing statistical similarity between two distributions.

FIG. 6 shows a real time calculated blood pressure probability distribution 605 of a current window compared with distribution 603 and distribution 607. Processor 15 calculates a dynamic sequential signal pattern index (or likelihood pattern), $$\text{Signal\_pattern}_{im} = \frac{\Phi_{im}}{\Phi_m} = \frac{\int_{mean_i - mean_m} \text{Overlapping\_area(distribution\_i, distribution\_m)}}{\int \text{area(distribution\_m)}}$$

where, $\Phi_{im}$ is the overlap area 610 comprising an integral of real time blood pressure probability distribution 605 and pre-determined distribution 603, $\Phi_m$ is the overlap area 612 comprising an integral of real time blood pressure probability distribution 605 and pre-determined distribution 607, $mean_i$ is a mean value of distribution 603 or 607 and $mean_m$ is the mean value of distribution 605. Processor 15 calculates an index value representing overlap between a current ongoing real time data distribution and a pre-determined data distribution. The larger the value of the Signal\_pattern$_{im}$ (likelihood pattern) overlap parameter, the more likely it is that the current data pattern is similar to a pre-determined signal pattern i.

Figure 7:
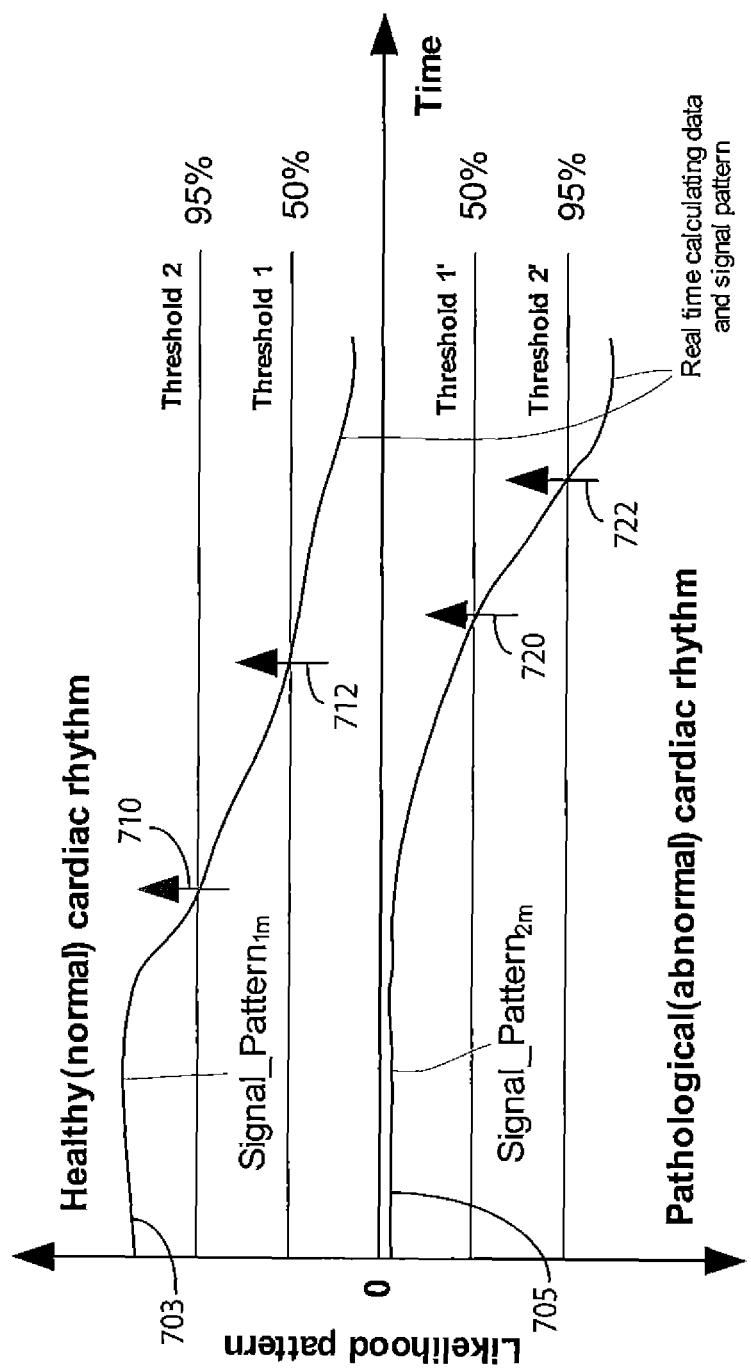
FIG. 7 illustrates blood pressure signal pattern analysis of normal and pathological blood pressure probability distributions, according to invention principles.

FIG. 7 illustrates blood pressure signal pattern analysis of normal and pathological blood pressure probability distributions comprising a simulation of a signal likelihood pattern index calculation to monitor and characterize a patient cardiac arrhythmia event indicating timing and severity. Data processor 15 calculates a Signal\_Pattern$_{1m}$, blood pressure pattern indicative value indicating degree of overlap between a first distribution (normal distribution) and an $m^{th}$ distribution which is a current distribution for example. Further, if a Signal_Pattern$_{1m}$, index value shows a change exceeding a predetermined threshold (e.g. a 50% change), processor 15 automatically generates an alarm identifying a detected event and severity. Comparing overlap between two distributions is typically sufficient to detect a cardiac event or arrhythmia. However, processor 15 comprises more than two distributions in one embodiment, to acquire more detailed information to indicate different levels of pathology such as an early stage or severe stage condition, for example. The quantitative distribution overlap comparison improves sensitivity and reliability of pathology detection.

Data processor 15 calculates a severity signal index pattern Signal_pattern$_m$ for two continuous signal pattern series. The calculated severity signal indices are shown in curves 703 and 705 indicating a likelihood pattern plotted against time. Curve 703 shows a severity signal index likelihood pattern compared to a normal healthy rhythm. Curve 705 shows a severity signal index likelihood pattern compared to a pathological cardiac rhythm. Processor 15 uses two separate thresholds for each of the signal patterns comprising 50% and 95% confidence levels. An emerging pathological cardiac rhythm is tracked and captured by monitoring the two signal pattern likelihood indices plotted in curves 703 and 705. Arrows 710 and 712 show the time that signal_Pattern$_{1m}$, of curve 703 of a current blood pressure signal pattern leaves a normal blood signal pattern with a 95% and 50% probability, respectively. Similarly, arrows 720 and 722 show the time that signal_Pattern$_{2m}$, of curve 705 of a pathological cardiac arrhythmia blood pressure signal pattern indicates a pathological pattern with a 50% and 95% probability, respectively.

Data processor 15 in one embodiment comprises an ANN unit that employs a 20 data sample window for continuous real time arrhythmia severity index calculation based on a blood pressure signal. The thresholds are indicative of different severity levels used to characterize the calculated blood pressure index (either a direct measurement and calculated index or an index output by an ANN unit) and categorize patient health status. Data processor 15 (or a user) adaptively selects the thresholds for detection and warning generation to quantify and characterize a blood pressure signal as indicating a cardiac arrhythmia rhythm, for example in response to data indicating a clinical application or procedure being performed.

FIG. 8 comprises a table listing blood pressure signals and associated derived parameters used for blood pressure analysis. In one embodiment, data processor 15 calculates a blood pressure signal pattern (likelihood pattern index) for different blood pressure signal measurements, derived calculation indices, and estimated indices using a combined model, comprising an ANN unit. The table shows blood pressure signal categories in column 803 (time domain, frequency domain, statistical, other) and associated parameters in column 805 used by data processor 15 in blood pressure pattern parameter calculation and cardiac condition diagnosis.

Figure 9:
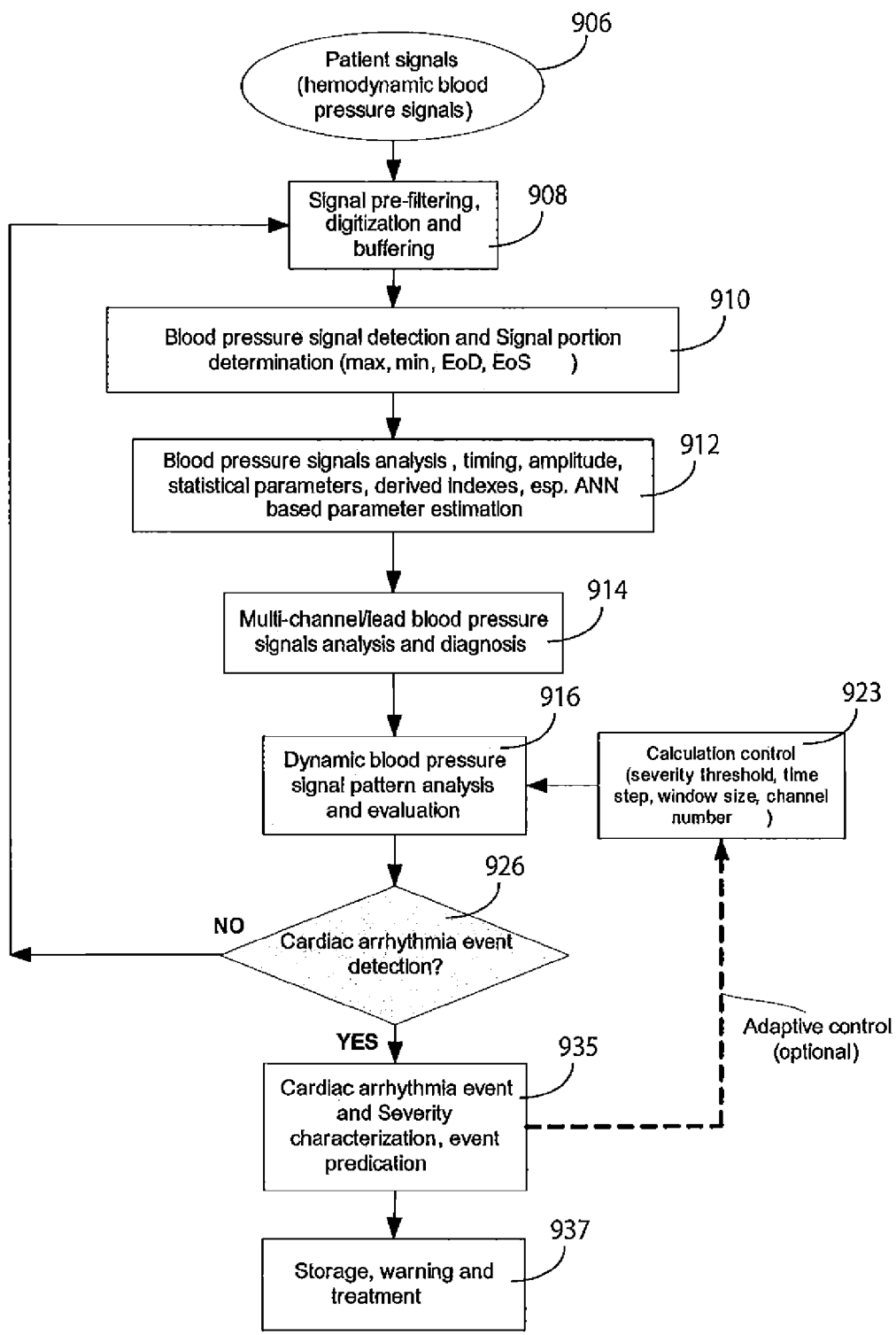
FIG. 9 shows a flowchart of a process performed by the system for monitoring and characterizing cardiac function based on hemodynamic blood signal pattern analysis, according to invention principles.

FIG. 9 shows a flowchart of a process performed by system 10 (FIG. 1) for monitoring and characterizing cardiac function based on hemodynamic blood signal pattern analysis. Data processor 15 (FIG. 1) buffers and digitizes a hemodynamic blood pressure signal received in step 906. Processor 15 in step 908 filters the sampled data using a filter adaptively selected in response to data indicating clinical application to remove patient movement and respiratory artifacts as well as power line noise. In step 910, data processor 15 detects blood pressure signal parameters and performs signal segmentation to determine a maximum and minimum point in the blood pressure cycle and EoD (end of diastolic) and EoS (end of systolic) points, for example. In step 912 processor 15 performs blood pressure signal analysis involving time domain amplitude and latency determination and identification of associated times in a heart cycle. Processor 15 also performs frequency domain spectrum analysis, calculates a statistical parameter of the blood pressure data (including mean, standard deviation, variability) and determines a blood pressure entropy indicative value. Processor 15 also provides different output parameters including output indices and estimated parameters using a combination analysis derived using an ANN unit and nonlinear calculation. Processor 15 also derives and selects at least two blood pressure probability data distributions including a normal status distribution and a cardiac arrhythmia status distribution.

Data processor 15 in step 914, performs the analysis of step 912 for blood pressure signals acquired from multiple channels and leads of an invasive basket catheter or multiple different catheters as well as non-invasively measured blood pressures. The calculated patient blood pressure signals related parameters derived from different cardiac signals, may have different sensitivity. In step 916, processor 15 calculates an overlap indicator indicating degree of overlap of first distribution data and second distribution data in a predetermined interval of the distributions. Processor 15 performs statistical analysis and blood pressure signal characterization to detect cardiac arrhythmias based on a dynamic blood pressure signal pattern (likelihood pattern) calculation by calculating overlap indicators signal_pattern1$_m$ and signal_pattern2$_m$. Processor 15 employs a pre-determined data sample shifting window size for signal pattern analysis. The window size is adaptively selected in response to blood pressure signal quality and detected signal noise level.

In step 926 data processor 15 employs mapping information, associating ranges of a calculated overlap indicator value or values derived from the overlap indicator value, with corresponding medical conditions (e.g., arrhythmias) in determining patient medical conditions, events and patient health status. If data processor 15 in step 926 determines a medical condition indicating cardiac impairment or another abnormality is identified, processor 15 in step 935 uses the mapping information in determining severity, type and location of a cardiac condition. Processor 15 in step 937 generates an alert message identifying the medical condition and abnormality and output processor 20 communicates the message to a user and stores data indicating the identified condition and associated calculated parameters in repository 17. Processor 15 also determines the severity and location of the condition.

Processor 15 in step 923 selects a signal channel of a multi-channel catheter for use as signal input and adaptively adjusts the number of samples in a calculation window used for calculation and adjusts the selected portions and ROI of a filtered signal and adjusts a threshold employed by processor 15 to improve medical condition detection. In the atrial arrhythmia analysis, processor 15 selects a severity threshold, calculation time step, monitored tissue location in response to user command or automatic system adaptive adjustment. The multi-channel patient signals include different lead signals or surface ECG signals or different channels (unipolar or bipolar) ICEG signals. If data processor 15 in step 926 does not identify a medical condition, the process is repeated from step 908.

System 10 (FIG. 1) continuously acquires and samples patient blood pressure waveforms. The system (automatically or in response to user command) selects one or multiple different parameters to be used. A time window (size is adaptively controlled) and is used to identify data samples for probability distribution determination. For example, system 10 in one embodiment uses maximum blood pressure amplitude for cardiac arrhythmia detection. At the beginning, normal heart blood pressure is acquired (e.g., 120, 118, 121, . . . mmHg) and data distribution N is derived. A shifting window is continuously moved for blood pressure distribution analysis. In response to a new set of data being within the shifting window (such as 130, 129, 133, . . . mmHg), a new data distribution, M, is derived. The system compares distribution N and M, by using the signal pattern definition and equation previously described and calculates a real time pattern overlap index value to show blood pressure changes. Warning and detection thresholds are also determined based on sensitivity and reliability.

A probability distribution as used herein may comprise a linear or nonlinear function. A distribution waveform is derived for each ROI portion of a blood pressure waveform. A distribution is derived for a pre-determined normal data set and a current acquired blood pressure data set (data within a time window). The probability function and distribution are used to analyze blood pressure data patterns. Different probability functions may be used including (discrete) a histogram probability function, binomial probability function, cumulative probability function and normal probability function.

Figure 10:
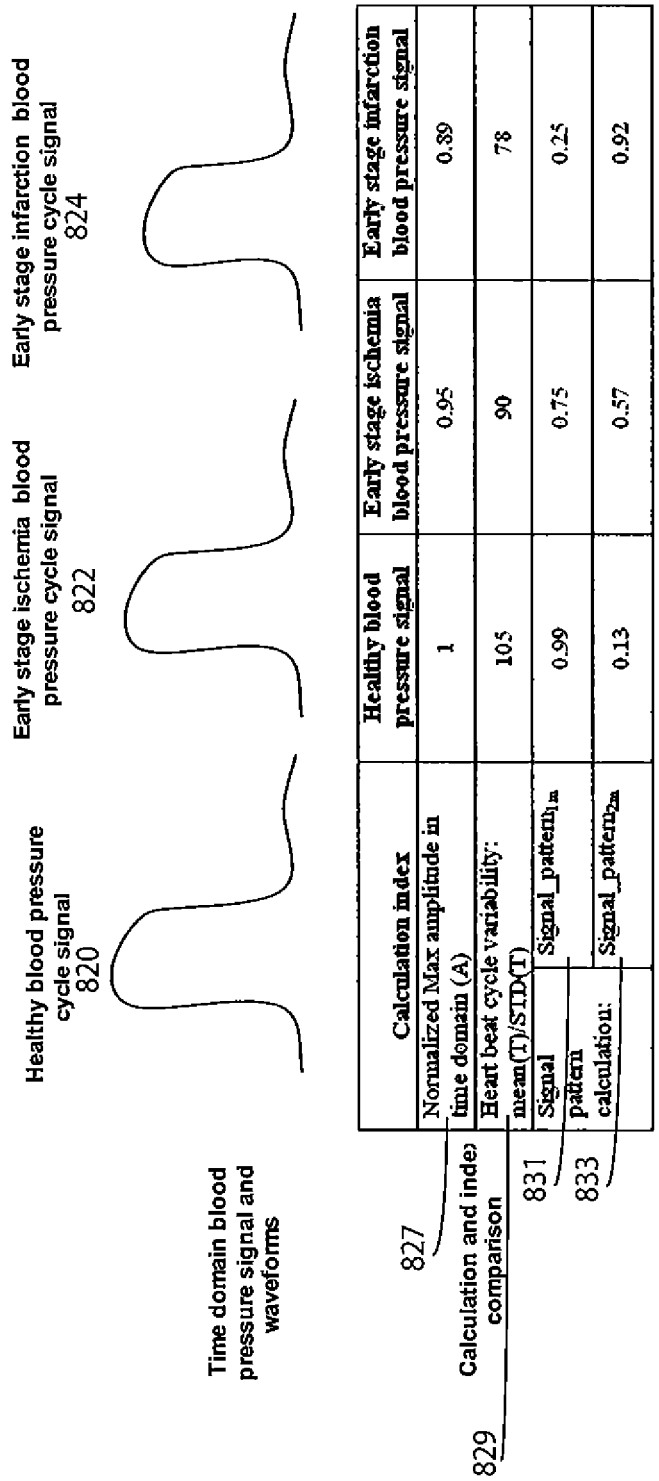
FIG. 10 shows simulation of data variation and variability calculation based blood pressure monitoring, according to invention principles.

FIG. 10 shows simulation of data variation and variability calculations concerning single channel intra-cardiac invasive blood pressure monitoring. System 10 (FIG. 1) analyzes invasive blood pressure signals as well as non-invasive or least invasive blood pressure data to monitor clinical events and cardiac pathologies within a heart, such as atrial fibrillation, atrial flutter and ventricle arrhythmias. Data processor 15 calculates variation and variability as previously described to accurately locate time of an event within a heart cycle and severity (including a trend) to provide early pathology detection. Additionally processor 15 performs statistical analysis, a hypothesis test and entropy analysis. Processor 15 analyzes pressure data (such as systolic and diastolic value series), statistical dynamic characteristics and blood pressure signal patterns. A blood pressure related trend is determined for early detection and prediction of patient pathologies and clinical events.

Different kinds of blood pressure data may be examined using variation and variability analysis. Non-invasive and invasive based blood pressure calculation and comparison improves quantification of data indicating pathology and events and identification of an abnormal vessel or an abnormal tissue location. Data processor 15 analyzes data representing a healthy blood pressure cycle waveform 820, an early stage ischemic blood pressure cycle waveform 822 and an early stage infarction blood pressure cycle waveform 824. Specifically, processor 15 analyzes blood pressure maximum amplitude change 827, heart beat cycle time duration variability 829 and derives overlap indicators signal_pattern1$_m$ 831 and signal_pattern2$_m$ 833 for waveforms, 820, 822 and 824. The heart beat cycle time duration variability 829 is determined as a ratio of mean cycle time duration (T) to standard deviation of mean cycle time duration (STD(T)). The overlap indicators signal_pattern1$_m$ 831 and signal_pattern2$_m$ 833 are used to compare waveforms 820, 822 and 824, with a previously recorded healthy waveform and infarction waveform.

The determined maximum amplitude values for healthy waveform 820, early stage ischemia waveform 822 and early stage infarction waveform 824 are 1, 0.95 and 0.89 respectively. The maximum amplitude change 827 between healthy and infarction waveforms is 11%. For blood pressure cycle length variability, the values (mean(T)/STD(T)) for waveforms 820, 822 and 824 are 105, 90, and 78 respectively indicating the maximum change between healthy and infarction waveforms is about 26%. Processor 20 analyzes two blood pressure signal patterns to characterize blood pressure change for different level myocardial arrhythmias by calculating signal_pattern1$_m$ and signal_pattern2$_m$, by comparison with previously determined healthy and infarction blood pressure signal distributions. For signal_pattern1$_m$, the signal pattern likelihood indices for healthy status, early ischemia and infarction are 0.99, 0.75 and 0.25. The maximum change of the signal_pattern1$_m$ is about 75%. For signal_pattern2$_m$, the signal pattern likelihood indices for healthy status, early ischemia and infarction are 0.13, 0.57 and 0.92. The maximum change of signal_pattern2$_m$ is about 600% derived by comparison with a benign (normal healthy blood pressure status) baseline signal. It can be seen that the overlap indicator comparison provides a more sensitive and reliable detection method than amplitude and cycle time variability analysis. The signal pattern analysis is used for qualitative indication of health status, quantitative early stage myocardial ischemia detection and early stage myocardial infarction detection. The signal pattern analysis is also utilized for quantitative characterization of myocardial ischemia events severity and level.

Data processor 15 detects peaks of a blood pressure waveform within received sampled data by synchronization of a heart electrical activity waveform and peak detection of a wave using a known peak detector and by identifying peaks of other waves by segmenting the signal represented by the sampled data into windows where the waves are expected and identifying the peaks within the windows. The Start point of a wave, for example, is identified by a variety of known different methods. In one method a wave start point comprises where the signal crosses a baseline of the signal (in a predetermined wave window, for example). Alternatively, a wave start point may comprise a peak or valley of signal. The baseline of the signal may comprise a zero voltage line if a static (DC) voltage signal component is filtered out from the signal. The data processor includes a timing detector for determining time duration between the signal peaks and valleys as indicated. The time detector uses a clock counter for counting a clock between the peak and valley points and the counting is initiated and terminated in response to the detected peak and valley characteristics.

Figure 11:
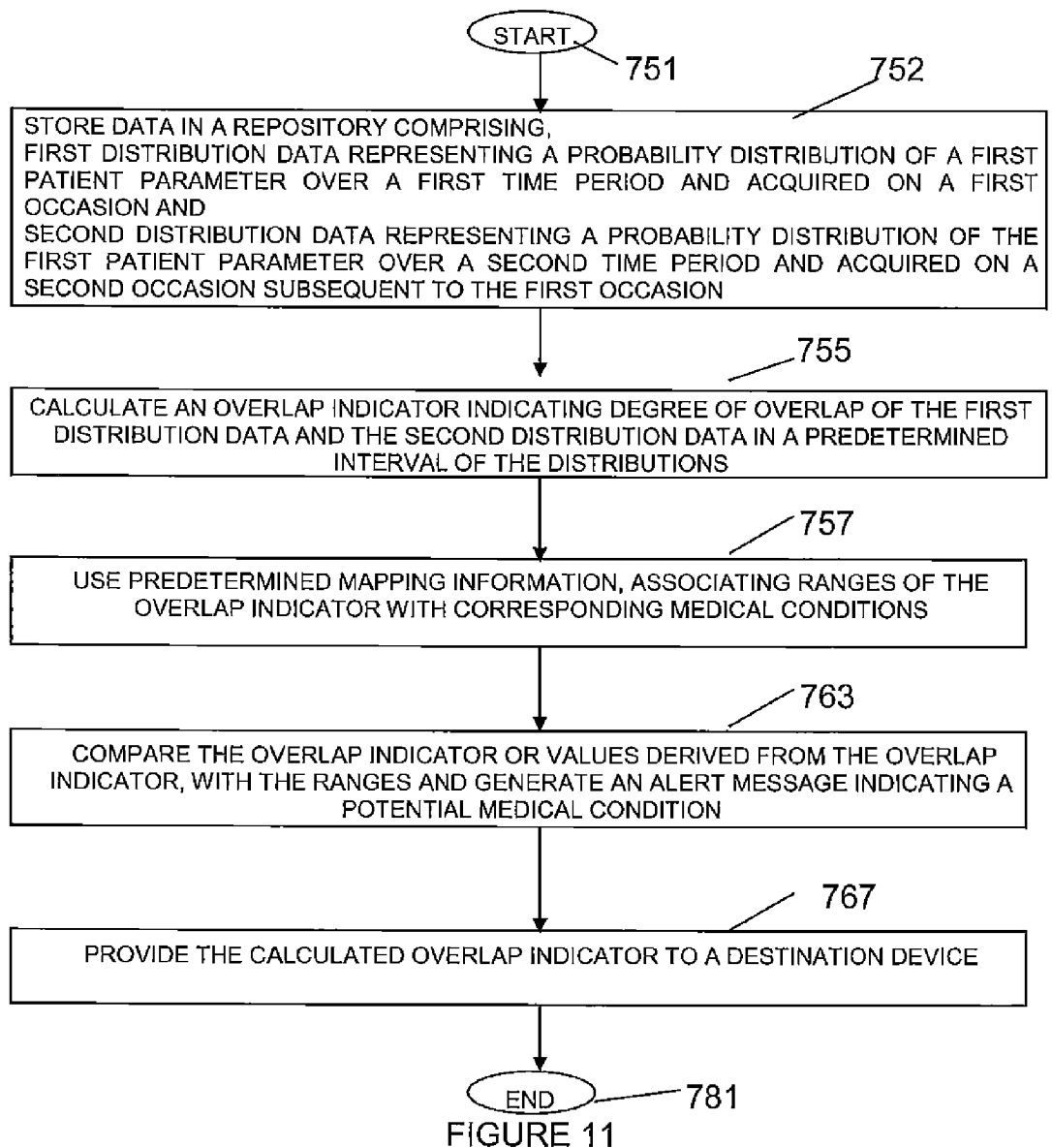
FIG. 11 shows a flowchart of a process used by a system for heart performance characterization and abnormality detection, according to invention principles.

FIG. 11 shows a flowchart of a process used by system 10 (FIG. 1) for heart performance characterization and abnormality detection. In step 752 following the start at step 751, data processor 15 stores in at least one repository 17, data comprising, first distribution data representing a probability distribution of a first patient parameter over a first time period and acquired on a first occasion and second distribution data representing a probability distribution of the first patient parameter over a second time period and acquired on a second occasion subsequent to the first occasion. The first patient parameter comprises a vital sign related parameter including at least one of, (a) a blood pressure related parameter, (b) a temperature related parameter, (c) an End of Diastolic blood pressure related parameter, (d) an End of Systolic blood pressure related parameter, (e) a blood pressure related parameter, (f) a temperature related parameter, (g) an End of Diastolic blood pressure related parameter, (h) an End of Systolic blood pressure related parameter, (i) an amplitude related characteristic, (j) a frequency related characteristic, (k) a timing related characteristic and (l) an energy related characteristic. In one embodiment, the first patient parameter comprises a weighted combination of different parameters derived using a function of the form, $$\sum_{j \in \Omega} \alpha_{ij}(t) \cdot C_j$$

for example, where index_i is an output index from an ANN (Artificial Neural Network) nonlinear model in processor 15, $C_j$ represents an input parameter of the ANN model, $\alpha_{ij}$ (t) represents weights, $\Omega$ represents the inputs.

The first distribution data represents a probability distribution of a first patient parameter associated with a normal healthy condition or pathology and the second distribution data represents a probability distribution of the first patient parameter associated with an abnormal condition indicating pathology. The first distribution and the second distribution comprise at least one of, (a) a uniform distribution, (b) a Cauchy distribution, (c) a T distribution, (d) an F distribution, (e) a Gamma distribution, (f) a Poisson distribution and (g) a Gaussian distribution. In one embodiment, the first distribution and the second distribution comprise different types of distribution.

In step 755 data processor 15 calculates an overlap indicator indicating degree of overlap of the first distribution data and the second distribution data in a predetermined interval of the distributions. The predetermined interval of the distributions comprises an interval substantially between a mean of the first distribution and a mean of the second distribution. Data processor 15 calculates the overlap indicator by integrating functions representing the first distribution and the second distribution to provide an integral value representing an area under the first distribution and the second distribution in the predetermined interval. Data processor 15 calculates the overlap indicator by dividing the integral value by a value representing an area under at least one of the first and second distributions in a predetermined interval. In one embodiment, the overlap indicator is of the form, $$\frac{\Phi_{im}}{\Phi_m} = \frac{\int_{mean_i - mean_m} \text{Overlapping\_area(distribution\_i distribution\_m)}}{\int \text{area(distribution\_m)}}$$

where, $\Phi_{im}$, is an overlapping area integration between first distribution m and second distribution I, $\Phi_m$ is the integration of data calculation m; $mean_i$ and $mean_m$ are the mean values of the data distributions.

In step 757 data processor 15 uses predetermined mapping information, associating ranges of the overlap indicator with corresponding medical conditions, and in step 763 compares the overlap indicator or values derived from the overlap indicator, with the ranges and generates an alert message indicating a potential medical condition. The predetermined mapping information associates ranges of the overlap indicator or values derived from the overlap indicator with particular patient demographic characteristics and with corresponding medical conditions and the data processor uses patient demographic data including at least one of, age weight, gender and height in comparing the overlap indicator or values derived from the overlap indicator with the ranges and generating an alert message indicating a potential medical condition. Output processor 20 in step 767 provides the calculated overlap indicator to a destination device. The process of FIG. 11 terminates at step 781.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication therebetween. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouth, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1-11 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. A system provides cardiac condition (e.g., arrhythmia) detection and characterization in response to blood pressure dynamic signal pattern analysis including determination of degree of overlap of blood pressure probability distributions derived from blood pressure data acquired at different times and occasions. Further, the processes and applications may, in alternative embodiments, be located on one or more (e.g., distributed) processing devices on a network linking the units of FIG. 1. Any of the functions and steps provided in FIGS. 1-11 may be implemented in hardware, software or a combination of both.

What is claimed is:

1. A system for heart performance characterization and abnormality detection, comprising:
a repository of data comprising,
first statistical distribution data representing a first statistical distribution of values of a first patient parameter over a first time period and acquired on a first occasion and
second statistical distribution data representing a second statistical distribution of values of said first patient parameter over a second time period and acquired on a second occasion subsequent to said first occasion;
a data processor configured to:
calculate a first mean of the first statistical distribution data;
calculate a second mean of the second statistical distribution data;
calculate an overlap indicator indicating degree of overlap of said first statistical distribution data and said second statistical distribution data only in a predetermined interval of the data distributed substantially between the first mean of the first statistical distribution data and the second mean of the second statistical distribution data;
use predetermined mapping information, associating ranges of said overlap indicator with corresponding medical conditions;
compare said overlap indicator or values derived from said overlap indicator, with said ranges; and
generate an alert message indicating a potential medical condition; and
an output processor configured to provide the calculated overlap indicator to a destination device.

2. The system according to claim 1, wherein
said first statistical distribution data represents a first statistical distribution of values of the first patient parameter associated with a normal healthy condition and
said second statistical distribution data represents a second statistical distribution of values of said first patient parameter associated with an abnormal condition indicating pathology.

3. A system according to claim 1, wherein
said first statistical distribution data represents a first statistical distribution of values of the first patient parameter associated with pathology and
said second statistical distribution data represents a second statistical distribution of values of the first patient parameter associated with pathology.

4. The system according to claim 1, wherein
said data processor calculates said overlap indicator by integrating functions representing said first statistical distribution and said second statistical distribution to provide an integral value representing an area under said first statistical distribution and said second statistical distribution in said predetermined interval.

5. A system according to claim 1, wherein
said data processor calculates said overlap indicator by dividing said integral value by a value a representing an area under at least one of the first and second statistical distributions in a predetermined interval.

6. A system according to claim 1, wherein said overlap indicator is of the form of, $$\frac{\Phi_{im}}{\Phi_m} = \frac{\int_{mean_i - mean_m} \text{Overlapping\_area(distribution\_i, distribution\_m)}}{\int \text{area(distribution\_m)}}$$

where, $\Phi_{im}$, is an overlapping area integration between first statistical distribution m and second statistical distribution I, $\Phi_m$ is the integration of data calculation m; $mean_i$ and $mean_m$ are the mean values of the statistical distributions.

7. A system according to claim 1, wherein
said first statistical distribution and said second statistical distribution comprise a Gaussian distribution.

8. A system according to claim 1, wherein
said first statistical distribution and said second statistical distribution comprise at least one of, (a) a uniform distribution, (b) a Cauchy distribution, (c) a T distribution, (d) an F distribution, (e) a Gamma distribution and (f) a Poisson distribution.

9. The system according to claim 1, wherein
said first statistical distribution and said second statistical distribution comprise different types of distribution.

10. The system according to claim 1, wherein
said first patient parameter comprises a vital sign related parameter.

11. The system according to claim 10, wherein
said first patient parameter comprises at least one of, (a) a blood pressure related parameter, (b) a temperature related parameter, (c) an End of Diastolic blood pressure related parameter and (d) an End of Systolic blood pressure related parameter.

12. The system according to claim 11, wherein
said first patient parameter comprises at least one of, (a) a blood pressure related parameter, (b) a temperature related parameter, (c) an End of Diastolic blood pressure related parameter and (d) an End of Systolic blood pressure related parameter.

13. The system according to claim 12, wherein
said first patient parameter comprises at least one of, (a) an amplitude related characteristic, (b) a frequency related characteristic, (c) a timing related characteristic and (d) an energy related characteristic.

14. The system according to claim 1, wherein
said predetermined mapping information associates ranges of said overlap indicator or values derived from said overlap indicator with particular patient demographic characteristics and with corresponding medical conditions and said data processor uses patient demographic data including at least one of, age weight, gender and height in comparing said overlap indicator or values derived from said overlap indicator with said ranges and generating an alert message indicating a potential medical condition.

15. The system according to claim 1, wherein
said first patient parameter comprises a weighted combination of different parameters.

16. The system according to claim 15, wherein said weighted combination of different parameters is derived using a function of the form, $$\sum_{j \in \Omega} \alpha_{ij}(t) \cdot C_j$$

where index _i is an output index from ANN (Artificial Neural Network) nonlinear model representing a parameter, $C_j$ represents an input parameter of the ANN model, $\alpha_{ij}$ (t) represents weights, n represents the inputs.

17. A system for heart performance characterization and abnormality detection, comprising:
   a repository of data comprising,
      first statistical distribution data representing a first statistical distribution of values of a first patient parameter over a first time period and acquired on a first occasion and
      second statistical distribution data representing a second statistical distribution of values of said first patient parameter over a second time period and acquired on a second occasion subsequent to said first occasion;
   a data processor configured to:
      calculate a first mean of the first statistical distribution data;
      calculate a second mean of the second statistical distribution data;
      calculate an overlap indicator indicating degree of overlap of said first statistical distribution data and said second statistical distribution data only in a predetermined interval of the data distributed substantially between the first mean of the first statistical distribution data and the second mean of the second statistical distribution data by determining an area under said first statistical distribution and said second statistical distribution in said predetermined interval;
      use predetermined mapping information, associating ranges of said overlap indicator with corresponding medical conditions;
      compare said overlap indicator or values derived from said overlap indicator, with said ranges; and
      generate an alert message indicating a potential medical condition; and
   an output processor configured to provide the calculated overlap indicator to a destination device.

18. A method employing at least one processing device for heart performance characterization and abnormality detection, comprising the activities of:
   storing data in at least one repository comprising,
      first statistical distribution data representing a first statistical distribution of values of a first patient parameter over a first time period and acquired on a first occasion and
      second statistical distribution data representing a second statistical distribution of values of said first patient parameter over a second time period and acquired on a second occasion subsequent to said first occasion;
   calculating a first mean of the first statistical distribution data;
   calculating a second mean of the second statistical distribution data;
   calculating an overlap indicator indicating degree of overlap of said first statistical distribution data and said statistical second distribution data only in a predetermined interval of the data distributed substantially between the first mean of the first statistical distribution data and the second mean of the second statistical distribution data;
   using predetermined mapping information, associating ranges of said overlap indicator with corresponding medical conditions;
   comparing said overlap indicator or values derived from said overlap indicator, with said ranges; and
   generating an alert message indicating a potential medical condition; and
   providing the calculated overlap indicator to a destination device.

* * * * *